(12) United States Patent
Situ et al.

(10) Patent No.: US 11,317,797 B2
(45) Date of Patent: May 3, 2022

(54) IDENTIFICATION OF CONTACT LENS WEARERS PREDISPOSED TO CONTACT LENS DISCOMFORT

(71) Applicant: Indiana University Research and Technology Corporation, Indianapolis, IN (US)

(72) Inventors: Ping Situ, Bloomington, IN (US); Carolyn Begley, Bloomington, IN (US); Trefford L. Simpson, Waterloo (CA)

(73) Assignee: Indiana University Research and Technology Corporation, Indianapolis, IN (US)

( * ) Notice: Subject to any disclaimer, the term of this patent is extended or adjusted under 35 U.S.C. 154(b) by 611 days.

(21) Appl. No.: 16/062,621

(22) PCT Filed: Dec. 20, 2016

(86) PCT No.: PCT/US2016/067678
§ 371 (c)(1),
(2) Date: Jun. 14, 2018

(87) PCT Pub. No.: WO2017/116826
PCT Pub. Date: Jul. 6, 2017

(65) Prior Publication Data
US 2019/0000312 A1    Jan. 3, 2019

Related U.S. Application Data

(60) Provisional application No. 62/271,797, filed on Dec. 28, 2015.

(51) Int. Cl.
*A61B 3/09* (2006.01)
*A61B 3/00* (2006.01)
(Continued)

(52) U.S. Cl.
CPC ............... *A61B 3/09* (2013.01); *A61B 3/00* (2013.01); *A61B 3/0025* (2013.01); *A61B 3/02* (2013.01); *A61B 3/101* (2013.01); *A61B 5/483* (2013.01)

(58) Field of Classification Search
CPC ....... A61B 3/0025; A61B 3/032; A61B 3/028; A61B 3/024; A61B 3/036; A61B 3/0008;
(Continued)

(56) References Cited

U.S. PATENT DOCUMENTS

| 5,230,347 A | 7/1993 | Weinstein et al. |
| 2007/0043140 A1 | 2/2007 | Lorenz et al. |

(Continued)

FOREIGN PATENT DOCUMENTS

WO    WO2017161404    *    3/2016

OTHER PUBLICATIONS

International Search Report and Written Opinion issued by the ISA/US, Commissioner for Patents, dated Mar. 14, 2017, for related International Application No. PCT/US2016/067678; 12 pages.
(Continued)

*Primary Examiner* — Collin X Beatty
*Assistant Examiner* — Grant A Gagnon
(74) *Attorney, Agent, or Firm* — Faegre Drinker Biddle & Reath LLP

(57) ABSTRACT

A method of determining a predisposition to contact lens discomfort in a patient is provided, comprising determining a detection threshold of the patient by delivering a cool mechanical stimulus to the cornea of the patient, optionally applying a series of cool mechanical stimuli to the cornea of the patient, and classifying the patient as being predisposed to contact lens discomfort if the detection threshold is at or below a cut-off value predetermined to be associated with
(Continued)

predisposition to contact lens discomfort and/or the patient does not adapt to the series of cool mechanical stimuli.

24 Claims, 6 Drawing Sheets

(51) Int. Cl.
    *A61B 3/02*     (2006.01)
    *A61B 5/00*     (2006.01)
    *A61B 3/10*     (2006.01)

(58) Field of Classification Search
CPC ......... A61B 3/0033; A61B 3/02; A61B 3/103; A61B 3/0091; A61B 3/0285; A61B 3/14; A61B 3/0058; A61B 3/113; A61B 3/12; A61B 3/18; A61B 3/0075; A61B 3/04; A61B 3/08; A61B 3/0041; A61B 3/022; A61B 3/005; A61B 3/063; A61B 3/102; A61B 3/152; A61B 3/066; A61B 3/09; A61B 3/10; A61B 5/04842; A61B 5/0496; A61B 2503/10; A61B 3/0083; A61B 3/06; A61B 3/1015; A61B 3/1035; A61B 3/11; A61B 3/111; A61B 3/112; A61B 3/1233; A61B 3/1241; A61B 5/16; A61B 5/163; A61B 5/165; A61B 5/7228; A61B 17/3417; A61B 1/00048; A61B 1/00193; A61B 2503/04; A61B 2503/08; A61B 2560/0214; A61B 3/00; A61B 3/0325; A61B 3/085; A61B 3/1005; A61B 3/101; A61B 3/1025; A61B 3/107; A61B 3/117; A61B 3/1225; A61B 3/145; A61B 3/154; A61B 3/16; A61B 5/0002; A61B 5/0013; A61B 5/002; A61B 5/0022; A61B 5/0066; A61B 5/0073; A61B 5/024; A61B 5/025; A61B 5/1036; A61B 5/1114; A61B 5/1124; A61B 5/117; A61B 5/12; A61B 5/14507; A61B 5/14546; A61B 5/161; A61B 5/18; A61B 5/4076; A61B 5/4088; A61B 5/4836; A61B 5/6803; A61B 5/6821; A61B 5/6898; A61B 5/7271; A61B 5/7475; A61B 90/39
USPC ........................................................ 351/222
See application file for complete search history.

(56) References Cited

U.S. PATENT DOCUMENTS

| | | |
|---|---|---|
| 2007/0168225 A1 | 7/2007 | Haider et al. |
| 2013/0090308 A1 | 4/2013 | Vehige et al. |
| 2013/0208246 A1 | 8/2013 | Huth et al. |
| 2014/0240671 A1 | 8/2014 | Korb et al. |
| 2019/0099071 A1* | 4/2019 | Ehrmann ............ G02B 27/0093 |

OTHER PUBLICATIONS

Chen, Jiangtao, et al., "A Role of Corneal Mechanical Adaptation in Contact Lens-Related Dry Eye Symptoms," *IOVS*, Mar. 2011, vol. 52, No. 3, available on the Internet at http://iovs.arvojournals.org/pdfaccess.ashx?url=/data/journals/iovs/932971/; pp. 1200-1205.

Situ, Ping, et al., "Conjunctival and Corneal Pneumatic Sensitivity is Associated with Signs and Symptoms of Ocular Dryness," *IOVS*, Jul. 2008, vol. 49, No. 7, available on the Internet at http://iovs.arvojournals.org/pdfaccess.ashx?url=/data/journals/iovs/932952/; pp. 2971-2976.

European Search Report and Search Opinion Received for EP Application No. 16882365.6, dated Oct. 8, 2019, 10 pages.

International Preliminary Report on Patentability received for PCT Patent Application No. PCT/US2016/067678, dated Jul. 12, 2018, 12 pages.

Martin-Montanez Vicente et al: "End-of-day dryness, corneal sensitivity and blink rate in contact lens wearers" Contact Lens and Anterior Eye, Stockton Contact Lens and Anterior Eye, Stockton Press, Basingstoke, GB, vol. 38, No. 3, Jan. 30, 2015 (Jan. 30, 2015), pp. 148-151.

Situ et al: "Eccentric variation of corneal sensitivity to pneumatic stimulation at different temperatures and with C0"2", Experimental Eye Research, Academic Press Ltd, London, vol. 85, No. 3, Aug. 18, 2007 (Aug. 18, 2007), pp. 400-405.

* cited by examiner

IDENTIFICATION OF CONTACT LENS WEARERS PREDISPOSED TO CONTACT LENS DISCOMFORT

RELATED APPLICATIONS

The present application is a U.S. National Stage Application of International Patent Application No. PCT/US2016/067678, filed Dec. 20, 2016, which claims the benefit of priority to U.S. Provisional Patent Application No. 62/271,797, titled "IDENTIFICATION OF CONTACT LENS WEARERS PREDISPOSED TO CONTACT LENS DISCOMFORT," filed Dec. 28, 2015, the entire disclosures of which are hereby expressly incorporated herein by reference in their entireties.

FIELD OF THE DISCLOSURE

The present disclosure relates generally to methods and devices for identifying contact lens wearers predisposed to contact lens discomfort, and more particularly to methods and devices for delivering a cool mechanical stimulus to the eye of the patient to determine a detection threshold and classifying the patient as being predisposed to contact lens discomfort if the threshold is less than or equal to a predetermined value.

BACKGROUND

Discomfort and dryness affect about 50% of the contact lens-wearing population and despite the advances in lens materials, contact lens discomfort ("CLD") is still the primary factor for abandonment of contact lens wear. While the causes of CLD are multifactorial and it is known that lens wear alters sensory responses of the ocular surface, the neural basis of the symptoms remains a mystery, in part because there is a poor correlation between the symptoms and clinical signs that might theoretically help to explain the symptoms. This lack of knowledge is an important problem because subjective measures of symptoms are often used to measure success, even though more quantitative, objective measures might be preferable. This has hindered the hypothesis-driven development and testing of new materials, solutions or other interventions designed to eliminate CLD.

Accumulating evidence suggests that adaptation and sensitization of the sensory system play an important role in contact lens-induced discomfort and dryness. Sensitization involves an enhanced response to a stimulus in the nervous system, leading to discomfort or pain. In contrast, neural adaptation is the decreased responsiveness to a repetitive and sustained stimulus over time and might partly be responsible for reducing lens awareness.

SUMMARY

In one embodiment, the present disclosure provides a method of determining a predisposition to contact lens discomfort in a patient, said method comprising: determining a detection threshold of the patient by delivering a cool mechanical stimulus to the cornea of the patient; optionally applying a series of cool mechanical stimuli to the cornea of the patient; and classifying the patient as being predisposed to contact lens discomfort if the detection threshold is at or below a cut-off value predetermined to be associated with predisposition to contact lens discomfort and/or the patient does not adapt to the series of cool mechanical stimuli. In one aspect of this embodiment, the cool mechanical stimulus is delivered by directing a cool fluid to the cornea of the patient. In a variant of this aspect, the cool fluid is a gas. In another variant, the cool fluid is a liquid. In another variant of this embodiment, the cool mechanical stimulus is a cool pneumatic stimulus and the series of cool mechanical stimuli is a series of cool pneumatic stimuli. In a further variation, the cool pneumatic stimulus is delivered by a pneumatic esthesiometer. In a still further variation, the cool pneumatic stimulus is delivered at about room temperature. In yet another variation, the cool pneumatic stimulus is delivered to the cornea at a controlled flow rate having a temperature of from about 20° C. to 30° C. from an air pulse source located at a controlled spaced-apart distance of from 1 mm to 10 mm from the cornea for a controlled duration of from 1 second to 5 seconds. In another variation, the cool pneumatic stimulus is delivered as ascending intensities of air pulse flow rates, with a pause between deliveries of different air pulse flow rates, until an air pulse flow rate elicits a positive psychophysical response from the patient, wherein said air pulse flow rate that elicits the positive psychophysical response from the patient is used to determine the patient's detection threshold. In another variation, the series of cool pneumatic stimuli is applied to the cornea of the patient and the patient is classified as being predisposed to contact lens discomfort if the patient does not adapt to the series of cool pneumatic stimuli. In a further variation, the series of cool pneumatic stimuli is applied at subthreshold intensity. In still a further variation, the series of cool pneumatic stimuli is applied at threshold intensity. In another variation, the series of cool pneumatic stimuli is applied at suprathreshold intensity. In another variation, the patient is prescribed initial contact lenses after the detection threshold is determined and the series of cool pneumatic stimuli is applied to the patient after the initial contact lenses have been worn by the patient for at least one day. In a still further variation, the method comprises prescribing contact lenses comprising a different design and/or material from the initial contact lenses if the patient does not adapt to the series of cool pneumatic stimuli. In another variant of this embodiment, the detection threshold or the patient's ability to adapt to the series of cool mechanical stimuli are determined prior to prescribing contact lenses to the patient. In another aspect, the patient is one of a neophyte contact lens wearer, a current contact lens wearer and a lapsed contact lens wearer. In yet another aspect, the patient as a subject in a clinical trial for a pre-marketed contact lens. In another aspect, the method comprises classifying the patient comprises inputting results of the determining step to a system comprising at controller configured to i) receive the results; ii) optionally receive data on whether the patient adapts to a series of cool mechanical stimuli administered to an ocular surface of the patient; and iii) classify the patient as being predisposed to contact lens discomfort if the patient's detection threshold is below a predetermined cut-off associated with predisposition to contact lens discomfort and/or if the patient does not adapt to the series of cool mechanical stimuli. In a variant of this aspect, the controller carries out the additional step of iv) outputting a recommendation for the patient's follow-up management based on the patient's classification. In a further variant, the patient is classified as being predisposed to contact lens discomfort and the recommendation for the patient's follow-up management comprises at least one of prescribing a premium lens to the patient, prescribing an ophthalmic drop that promotes ocular comfort, and scheduling a follow-up visit for the patient.

In another embodiment, the present disclosure provides an analysis system comprising: an esthesiometer comprising a source of fluid, a fluid flow rate controller coupled to the source of fluid, a tip coupled to the flow rate controller adapted to deliver a cool mechanical stimulus to an ocular surface of a patient, and a user input device by which patient responses can be signaled; and a controller in communication with the flow rate controller to execute a test process including: producing a stimulus according to a detection threshold test protocol for detecting a threshold of a cool mechanical stimulus administered to an ocular surface of the patient, and storing patient responses received at the user input device during execution of the detection threshold test protocol, the sequence controller determining the patient's detection threshold based on the stored patient responses for the detection threshold test protocol, optionally producing a series of stimuli according to an adaptation test protocol for determining whether the patient adapts to a series of cooling mechanical stimuli administered to the ocular surface of the patient, and storing patient responses received at the user input device during execution of the adaptation test protocol, the controller determining whether the patient adapts to the series of cooling mechanical stimuli based on the stored patient responses for the adaptation test protocol; and generating data for classifying the patient as being predisposed to contact lens discomfort if the patient's detection threshold is below a predetermined cut-off associated with predisposition to contact lens discomfort and/or if the patient does not adapt to the series of cooling mechanical stimuli. In one aspect of this embodiment, the fluid is a gas, the cool mechanical stimulus is a cool pneumatic stimulus, and the series of cooling mechanical stimuli is a series of pneumatic cooling stimuli.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein.

Figure 1:
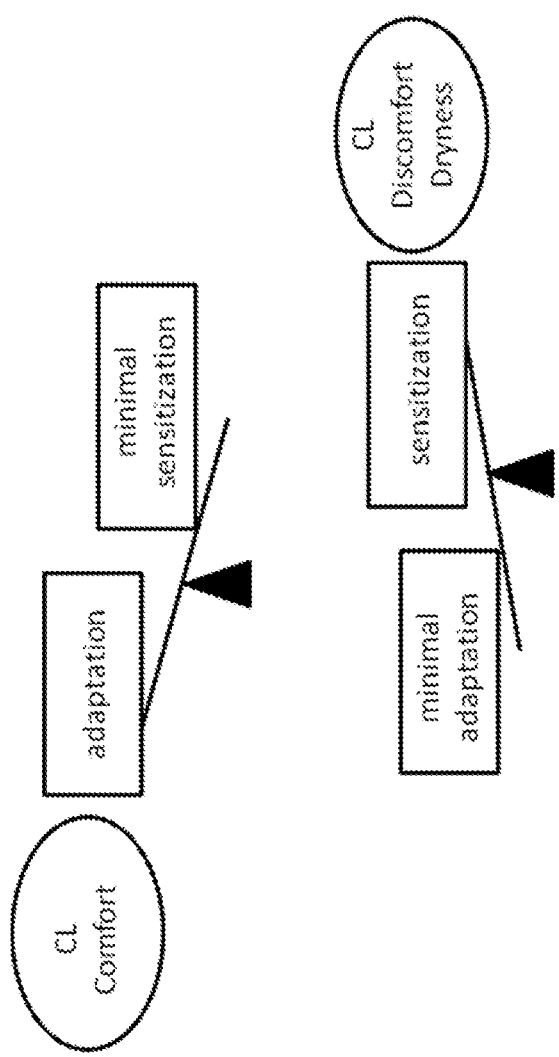
FIG. 1 is a conceptual diagram of the sensory response to contact lens wear.

Corresponding reference characters indicate corresponding parts throughout the several views. Although the drawings represent embodiments of the present invention, the drawings are not necessarily to scale and certain features may be exaggerated in order to better illustrate and explain the present invention. The exemplification set out herein illustrates an embodiment of the invention, in one form, and such exemplifications are not to be construed as limiting the scope of the invention in any manner.

DETAILED DESCRIPTION

The embodiments disclosed below are not intended to be exhaustive or to limit the invention to the precise forms disclosed in the following detailed description. Rather, the embodiments are chosen and described so that others skilled in the art may utilize their teachings.

Referring now to FIG. 1, a hypothesis is depicted that the main sensory cause of contact lens-induced symptoms of dryness and discomfort is an imbalance of the sensory response. A test of the hypothesis is to determine whether a difference in the balance between sensitization and adaptation occurs in symptomatic and asymptomatic contact lens wearers. The present disclosure studied a symptomatic group and an asymptomatic group and determined that they generally exhibited different sensory responses to a cooling mechanical stimulus as well as the ability to adapt to repetitive cooling mechanical stimuli. As used herein, the phrase "mechanical stimulus" is intended to mean mechanical forces (e.g., a stimulus that could potentially result in membrane deformation) that activate polymodal and/or mechanoreceptors. The phrase "cool [or cooling] mechanical stimulus" is intended to mean mechanical stimuli that activate both cold sensitive receptors and polymodal and/or mechanoreceptors. As described below, findings of the study unambiguously support the hypothesis that sensitization and adaptation play important roles in contact lens-induced symptoms and lead to methods and systems for predicting a patient's predisposition to contact lens discomfort.

In one embodiment of the disclosure, a method is provided for delivering a cool mechanical stimulus to an ocular surface (e.g., cornea or conjunctiva) of the patient to determine the patient's detection threshold. As used herein, the term "detection threshold" refers to the lowest level of a cooling mechanical stimulus that is detected by the patient. The method optionally comprises administering a series of cool mechanical stimuli to an ocular surface of the patient. The patient is classified as being predisposed to contact lens discomfort if the detection threshold is at or below a cut-off value predetermined to be associated with predisposition to contact lens discomfort or if the patient does not adapt to the series of cool mechanical stimuli. In some examples, the mechanical stimulus may be delivered by directing a cool fluid to an ocular surface of the patient by an esthesiometer adapted for delivery of a fluid to ocular tissue at controlled intensity (e.g., flow rate) and temperature. In one example, the cool fluid is a gas administered by a pneumatic esthesiometer. In another example, the cool fluid is a liquid administered by a liquid jet esthesiometer. In other examples, the mechanical stimulus may be administered by a probe that comes into direct contact with the ocular surface of the patient.

As used herein, a cool mechanical stimulus has a temperature less than 33° C., which is the temperature of the ocular surface. The use of a cooling mechanical stimulus allows significant differentiation between the detection thresholds of symptomatic patients and asymptomatic patients, whereas a purely mechanical stimulus (i.e., a mechanical stimulus applied at corneal temperature) may not provide significant differentiation. In various examples, the temperature of the mechanical stimulus may be less than 30° C. or less than 25° C. In certain examples, the temperature of the mechanical stimulus may be from about 15° C. to about 20° C., or from about 20° C. to about 25° C. In a specific example, the temperature of the mechanical stimulus is about room temperature (typically about 22° C.). Thus, the mechanical esthesiometer may also comprise a temperature control for adjusting the temperature of the fluid discharged from the nozzle.

Figure 6:
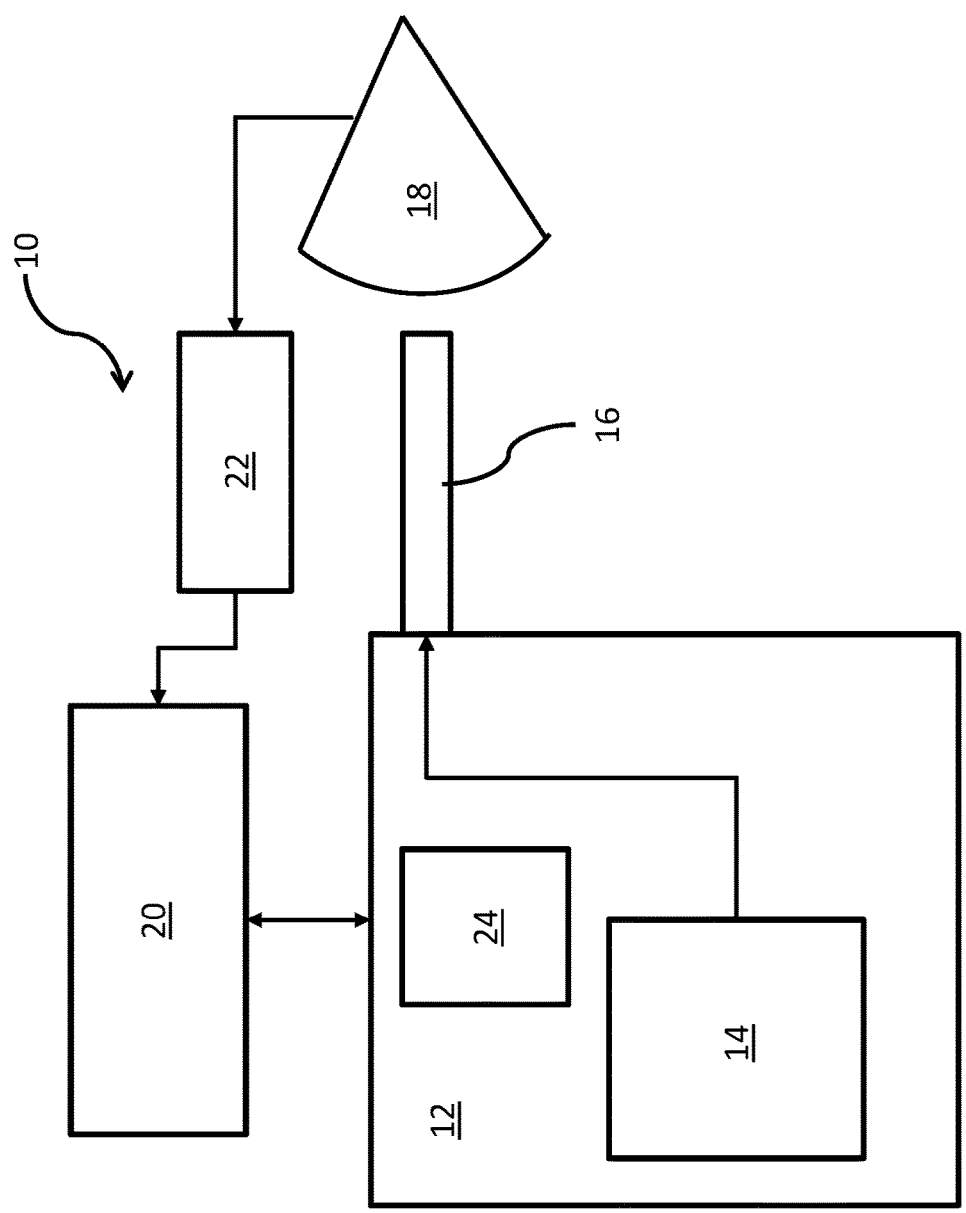
FIG. 6 is a conceptual diagram of a system for delivering a cool pneumatic stimulus.

The present disclosure is described herein with reference to a pneumatic esthesiometer. However, it will be appreciate that other means of delivering a cool mechanical stimulus to an ocular surface can be used. In the specific example of system 10 depicted in FIG. 6, the cool mechanical stimulus is delivered by a pneumatic esthesiometer 12 comprising a pressurized air source 14 and a nozzle or tip 16 fluidly connected to the pressurized air source from which air pulses can be discharged at a controlled flow rate toward the ocular surface of a patient's eye 18. For example, the system 10 may be capable under the control of a controller 20 of providing controlled air flow rates ranging from 0 ml/min to 200 ml/min. Suitable pneumatic esthesiometers, also known as Belmonte esthesiometers or gas esthesiometers, are well-known to those skilled in the art.

Air discharged by the pneumatic esthesiometer may have the same make-up as ambient air. In other examples, the discharged air may have a make-up that is different from ambient air, for example, it may have a higher concentration of $CO_2$ than ambient air. Thus, as used herein, the term "air" is intended to be synonymous with the term "gas." In a specific example, the pneumatic stimulus is administered to the patient's cornea at a controlled flow rate having a temperature of from 20° C. to 30° C. from an air pulse source located at a controlled spaced-apart distance of from 1 mm to 10 mm from the ocular surface for a controlled duration of from 1 second to 5 seconds. In a specific example, the air pulse source is located at a controlled spaced-apart distance of from about 4 to 6 mm from the cornea of the patient, and the pneumatic stimulus is administered for a duration of about 2 seconds.

A patient's detection threshold may be determined by measuring a psychophysical response of the patient to at least one air pulse of predetermined flow rate and duration which is delivered to the patient's ocular surface from an air pulse source located in non-contacting proximity to the ocular surface of the patient's eye. In a specific example, the air pulse is directed at the patient's cornea. A minimum magnitude of air pulse intensity that elicits a positive pyschophysical response of the patient is determined. In other words, the lowest flow rate of cool air that is detectable by the patient is the patient's detection threshold. In one example, the detection threshold is determined by subjecting an ocular surface of the patient to air pulses delivered at ascending intensities of air pulse flow rates, with a pause between deliveries of different air pulse flow rates, until a positive psychophysical response is elicited from the patient after the delivery of an air pulse at an air pulse flow rate, which is determined to be the detection threshold. As used herein, a pause between deliveries of different air pulse flow rates may be a temporary decrease in the air pulse flow rate prior to delivery of the next higher intensity of air pulse flow rate, or it may be a temporary cessation of air flow. The initial air pulse is delivered to the patient at a flow rate that is undetectable, for example at about 30 ml/min, with the air-flow rate incrementally increased with each subsequent pulse until it is detected by the patient. In a specific example, the ascending method of limits is used with a randomly selected initial level of stimulus and an increment in flow rate of 10 ml/min.

Detection thresholds may be determined by the average flow rate of the first three reports of the stimulus detected by the patient. For example, once a patient reports stimulus detection, the flow rate may be dropped to a lower intensity and then increased again until the patient reports stimulus detection again. This is then repeated a third time, and the average flow rate of the three stimuli detected by the patient is taken to be the patient's detection threshold. The patient may self-report the occurrence of the psychophysical response. In other examples, a psychophysical response-detecting device may detect the occurrence of the psychophysical response of the patient.

A patient may be classified as being predisposed to contact lens discomfort if the patient's detection threshold is at or below a cut-off value predetermined to be associated with predisposition to contact lens discomfort. A cut-off value associated with predisposition to contact lens discomfort may be predetermined for a particular pneumatic esthesiometer and method by a clinical study that determines the mean detection thresholds for a group of patients symptomatic for contact lens discomfort and a group of patients asymptomatic for contact lens discomfort. The predetermined cut-off value is selected as a value that is less than the mean detection threshold of the asymptomatic group and no less than the mean detection threshold of the symptomatic group. As will be appreciated, the predetermined cut-off values may differ depending on the method used in the clinical study. For example, method variables may include temperature of cool pneumatic stimulus, duration of stimulus, duration between stimuli, etc.

After a patient's detection threshold is determined, the method of determining a predisposition to contact lens discomfort in a patient may optionally comprise applying a series of cool pneumatic stimuli to the ocular surface of the patient and determining whether the patient adapts to the series of cool pneumatic stimuli. The series may comprise a number of air pulses of equal duration and intensity. The duration of each air pulse in the series may be about 1 second up to about 5 seconds, or about 1 to 3 seconds. In a specific example, each air pulse in the series is about 2 seconds. The duration between each air pulse may be about 5 to 30 seconds, or 5 to 15 seconds. In a specific example, the duration between each air pulse is about 10 seconds.

The intensity of each air pulse in the series may be equal to the patient's previously determined detection threshold, or it may be below or above the patient's detection threshold (i.e. subthreshold or suprathreshold, respectively). For example, the pneumatic cooling stimuli may be administered to the patient at a constant intensity between 50% and 150% of the patient's pre-determined detection threshold. In a specific example, each air pulse in the series has a subthreshold intensity that is about 25% below the patient's detection threshold. In another specific example, each air pulse in the series has a suprathreshold intensity that is about 25% above the patient's detection threshold.

The patient may rate the intensity of each air pulse after it is administered. In one example, a 5-point intensity rating scale is used where 0=no stimulus detected, 1=very mild, 2=mild, 3=moderately strong, and 4=strong. A patient having an average intensity rating for air pulses administered at the end of the series that is lower than the patient's average intensity rating for air pulses administered at the beginning of the series, indicates that the patient adapted to the series of cool pneumatic stimuli. In this circumstance, the patient may be classified as not being predisposed to contact lens discomfort. Conversely, a patient having an average intensity rating for air pulses administered at the end of the series that is the same or higher than the patient's average intensity rating for air pulses administered at the beginning of the series, indicates that the patient did not adapt to the series of cool pneumatic stimuli. For example, a patient may be subjected to a series of 20 threshold level air pulses. If the patient's average intensity rating for the first 4 pulses of air equals 1, and the patient's average intensity rating for the last 4 pulses of air equals 1.3, then the patient did not adapt to the series of cool pneumatic stimuli. In such example, the patient may be classified as being predisposed to contact lens discomfort when the patient's detection threshold is below a predetermined cut-off associated with predisposition to contact lens discomfort and the patient does not adapt to the series of cool pneumatic stimuli.

In one example, the patient may be prescribed initial contact lenses after the detection threshold is determined and before the series of cool pneumatic stimuli is applied. In such example, the patient may wear the initial contact lenses for at least one day up to about one month, in accordance with the prescription, prior to returning for a follow-up visit with the eye-care professional during which the series of cool pneumatic stimuli is applied. In this example, the patient may be prescribed contact lenses comprising a different design and/or material from the initial lenses if the patient is determined to be non-adaptive to the series of cool pneumatic stimuli. In other examples, the detection threshold and the patient's ability to adapt to the series of cool pneumatic stimuli are determined at the same office visit prior to prescribing contact lenses to the patient. In some examples, the patient is a "neophyte" contact lens wearer, meaning that the patient has never worn contact lenses. In other examples, the patient is a current contact lens wearer. In another example, the patient may be a "lapsed" contact lens wearer, meaning the patient has worn contact lenses for a period of time, but discontinued wear due to contact lens discomfort.

The methods described herein advantageously enable the eye-care professional to provide better patient care and management, leading to higher patient retention, among other things. The eye-care professional may provide different aftercare scheduling or advice to a patient determined to be predisposed to contact lens discomfort compared to a patient that is not predisposed to contact lens discomfort. For example, a patient that is determined to be predisposed to contact lens discomfort may be prescribed a more comfortable, premium lens and/or an eye treatment, such as wetting eye drops, that promotes ocular comfort. Conversely, a patient that is determined to not be predisposed to contact lens discomfort may be prescribed a more affordable contact lens. Further, a patient determined to be predisposed to contact lens discomfort may be scheduled for a follow-up appointment sooner than if the patient had been determined to not be predisposed to contact lens discomfort. In some examples, the patient has worn contact lenses, referred to as "habitual lenses", six or more hours/day for at least one week just prior to testing by the method described herein. In such an example, the patient may be prescribed contact lenses comprising a different design and/or material from the habitual lenses if the patient is determined to be predisposed to contact lens discomfort.

The methods described herein are also advantageous in that they provide for better characterization of subjects recruited for clinical trials of a pre-marketed contact lens or a contact lens in development, which in turn may lead to better predictability about the potential commercial success of a new contact lens material or design. For example, a clinical trial designed to compare the comfort of a new contact lens material or design in comparison to a preexisting commercial contact lens may use only subjects determined to be predisposed to contact lens discomfort. In another example, a clinical trial may evaluate the comfort of a contact lens by a first group of subjects determined to be predisposed to contact lens discomfort compared to a second groups of subjects determined to not be predisposed to contact lens discomfort.

In some examples, classifying the patient comprises inputting results of the determining step to one or more computer systems including, for example, controller 20, comprising at least one processor and a non-transitory computer-readable medium, wherein the computer-readable medium is configured to have patient data inputted and stored therein and includes a stored program comprising a set of instructions performed by the at least one processor for carrying out steps which comprise i) receiving data on a determination of the patient's detection threshold; ii) optionally receiving data on whether the patient adapts to the series of cooling pneumatic stimuli administered to an ocular surface of the patient; and iii) classifying the patient as being predisposed to contact lens discomfort if the patient's detection threshold is below a predetermined cut-off associated with predisposition to contact lens discomfort and/or if the patient does not adapt to the series of cooling pneumatic stimuli. In a specific example, the processor carries out the additional step of iv) outputting a recommendation for the patient's follow-up management based on the patient's classification. For example, a patient may be classified as being predisposed to contact lens discomfort and the recommendation for the patient's follow-up management may be selected from prescribing a premium lens to the patient, or prescribing an ophthalmic drop that promotes ocular comfort, or scheduling a follow-up visit for the patient, or any combination thereof.

As described above with reference to FIG. 6, an analysis system for carrying out the above-described methods may comprise a pneumatic esthesiometer and a sequence controller in communication with the pneumatic esthesiometer for executing a detection threshold test protocol and optionally an adaptation test protocol. The pneumatic esthesiometer comprises a pressurized source of gas, a gas flow rate controller coupled to the source of gas, a tip coupled to the flow rate controller adapted to deliver a cool mechanical stimulus to an ocular surface of a patient, and a user input device 22, such as a button box, by which patient responses can be signaled. The esthesiometer may additionally comprise a temperature controller 24 for controlling the temperature of the gas at the tip. The sequence controller 20 (e.g., state machine implemented by a programmed general or special purpose data processor, by a programmable logic device, or by other logic processor or circuit devices) is in communication with the flow rate controller 12 and optionally other controllable elements of the esthesiometer such as the temperature controller, and executes a test process including: producing a stimulus according to a detection threshold test protocol for detecting a threshold of a cool mechanical stimulus administered to an ocular surface of the patient, and optionally producing a series of stimuli according to an adaptation test protocol for determining whether the patient adapts to a series of cooling mechanical stimuli administered to the ocular surface of the patient. The patient responses are received at the user input device 22 and stored at least temporarily during execution of the test protocols, and the sequence controller 20 generates data (e.g. a tag associated with a patient record, a message displayed on a user interface, a message transmitted to a computer, etc.) classifying the patient as being predisposed to contact lens discomfort if the patient's detection threshold is below a predetermined cut-off associated with predisposition to contact lens discomfort and/or if the patient does not adapt to the series of cooling mechanical stimuli. In one example, a state machine implementing the sequence controller 20 can be characterized by a plurality of logical states, including one or more states in which parameters for stimuli are set, and one or more logical states in which the esthesiometer is caused to deliver stimuli according to the current parameters. The state machine defines logical rules for transition between the logical states based on the test protocol or test protocols, and based on user response data, input signals provided by an operator, or both. The user input device 22 by which operator input signals and patient response signals can be provided can be implemented using a keyboard, a mouse, a touch screen, a microphone, a button box and other types of devices used to provide input to computers and logic circuits, and combinations thereof.

The following Examples illustrate certain aspects and advantages of the present disclosure, which should be understood not to be limited thereby.

EXAMPLE 1

Determination of Threshold Levels of Detection of a Cool Pneumatic Stimulus in Symptomatic, Asymptomatic, and Non-Contact Lens Wearers Subjects: Sixty-four participants comprising 24 symptomatic/intolerant, 25 asymptomatic lens wearers and 15 non-contact lens wearing normal controls completed the study. They were between 18 to 45 years of age. 47 and had no history of systemic diseases and/or were not using any systemic or topical medication that would affect ocular health. Slit-lamp biomicroscopy examination was undertaken to exclude clinically significant lid, conjunctival or corneal abnormalities other than the clinical signs of dry eye. Contact lens wearers were further classified into symptomatic and asymptomatic group using the criteria listed in Table 1.

TABLE 1

|  | Asymptomatic | Symptomatic |
|---|---|---|
| Reported comfortable lens wear time (CWT) | >10 hours & minimal reduction in comfort over the course of the day (i.e. lens wearing time - CWT < 1 hour) | <8 hours & a noticeable reduction in comfort over the course of the day |
| Contact Lens Dry Eye Questionnaire-8 (CLDEQ-8) score | <14 | ≥14 |

Sensitivity measurement: Corneal detection thresholds were estimated using a computer-controlled Belmonte pneumatic esthesiometer developed at Indiana University. The esthesiometer is a dual chamber mechanical, chemical ($CO_2$) and thermal pneumatic device with computer control of flow rate, % $CO_2$ and temperature and computerized collection of subject responses. A temperature sensing circuit provides feedback to maintain a steady stimulus temperature independent of air-flow and ambient temperature. A calibrated video camera continuously monitored the distance between and orthogonal alignment of the tip of the esthesiometer and the ocular surface.

Detection thresholds were measured on the left eye only, at least three hours after subjects awoke. A training session was conducted at the screening visit. Subjects were instructed to view a fixation target and the tip of the esthesiometer was set 5 mm from the corneal surface. The stimuli, consisting of a series of air pulses at room temperature (20° C., an air stimulus with a cooling effect) with flow varying from 0 to 200 ml/min, were delivered to the central cornea. The subjects were informed that they could blink freely and also to close their eyes or look down between stimuli, and that they could interrupt the trials whenever they chose to. The stimulus duration was 2 seconds, with a computer-generated warning tone so that subjects might blink before the stimulus and then view the fixation target during stimulus presentation. Using the ascending method of limits with a randomly selected initial level of stimulus and an increment in flow rate of 10 ml/min, detection thresholds were determined by the average flow rate of three first reports of the stimulus presence.

Following successful screening and training, subjects returned for baseline threshold estimation (BL-1) and threshold estimates were repeated under the same conditions within a week (BL-2). Subjects then stopped wearing their contact lenses for approximately two weeks and thresholds were measured again (NL). Finally the contact lens group wore their lenses again for two weeks, after which thresholds were estimated (CL). Each experimental and control participant therefore had thresholds measured four times.

On the day before each measurement session, subjects in the contact lens wearer group wore their habitual lenses for approximately three to six hours. The non-contact lens wearing group was instructed to be awake for three to six hours before each measurement session. Prior to the third measurement session (NL), none of the participants used contact lenses and all were instructed to be awake for three to six hours before the study visit.

Data were analyzed using mixed models and repeated measures ANOVA in SPSS 22 (IBM SPSS) and $p \leq 0.05$ was considered to be statistically significant. Detection thresholds were outcomes, with groups, visits and their interactions as predictors. To minimize the effects of violating assumptions about data sphericity for repeated-measures ANOVA, Huynh-Feldt corrected p values were reported. Although the analyses of esthesiometry data were done on thresholds, the term sensitivity, that is the reciprocal of threshold, is also used in discussing the study outcomes since it is a commonly used term.

Results: Participant characteristics for each group are summarized in Table 2.

TABLE 2

|  |  | Control | Asymptomatic | Symptomatic |
|---|---|---|---|---|
| Number of Subjects |  | 15 | 25 | 24 |
| Age (years) |  | 25 ± 3 | 23 ± 2 | 23 ± 4 |
| Female:Male |  | 8:7 | 17:8 | 18:6 |
| Refractive error | Sph (D) | −1.15 ± 2.33 | −3.35 ± 1.71 | −3.66 ± 1.57 |
|  | Cyl (D) | −0.57 ± 0.44 | −0.50 ± 0.50 | −0.66 ± 0.65 |
| K readings | fat K (D) | 43.52 ± 1.25 | 43.27 ± 1.43 | 43.31 ± 1.47 |
|  | steep K (D) | 44.38 ± 1.48 | 43.95 ± 1.46 | 44.43 ± 1.73 |
| Corneal cylinder |  | −1.10 ± 0.65 | −0.78 ± 0.32 | −1.20 ± 0.77 |
| Lens wearing time | hrs/day | n/a | 14.1 ± 1.7 | 10.1 ± 3.9 |
|  | days/wk |  | 5.9 ± 1.4 | 5.4 ± 1.7 |

TABLE 2-continued

|  | Control | Asymptomatic | Symptomatic |
|---|---|---|---|
| CWT (hrs/day) | n/a | 13.9 ± 1.8 | 5.1 ± 1.7 |
| TF break-up time (sec.) | 12.20 ± 6.19 | 10.42 ± 7.08 | 6.45 ± 3.25 |
| CLDEQ-8 score | n/a | 7.2 ± 3.8 | 22.4 ± 3.8 |

Figure 2:
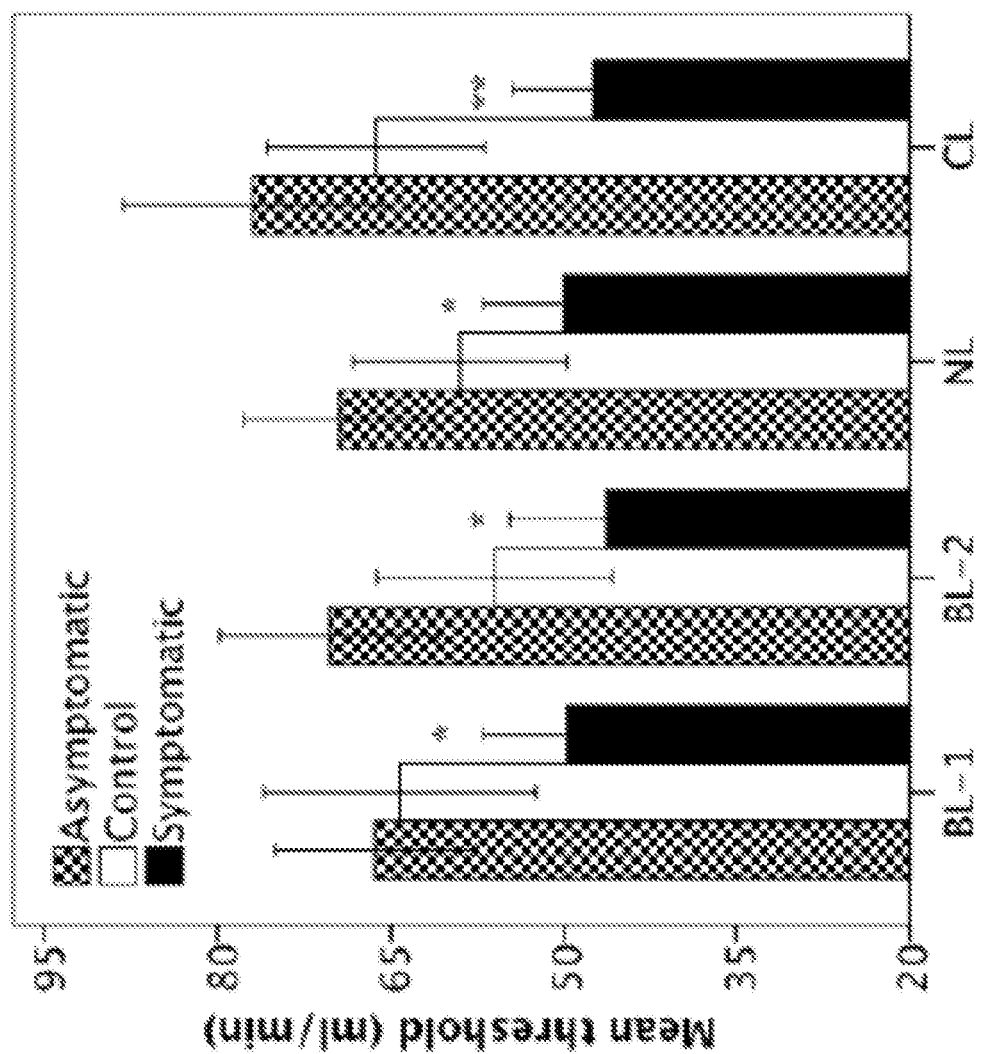
FIG. 2 is a graph of differences in mean detection thresholds between study groups.

Corneal thresholds for detection of pneumatic stimuli at room temperature for each measurement session are summarized in Table 3 and depicted in FIG. 2.

TABLE 3

| Visit | Control | Asymptomatic | Symptomatic |
|---|---|---|---|
| BL-1 | 64.2 ± 21.4 | 66.3 ± 21.0 | 49.7 ± 17.4 |
| BL-2 | 56.0 ± 18.3 | 70.3 ± 23.0 | 46.3 ± 20.0 |
| NL | 59.0 ± 16.9 | 69.5 ± 20.1 | 50.1 ± 16.5 |
| CL | 66.2 ± 17.0 | 77.0 ± 27.3 | 47.5 ± 16.3 |

Generally the symptomatic group was the most sensitive (i.e., had the lowest threshold), the asymptomatic were the least sensitive and the controls' sensitivity was between the two lens wearing groups. There were significant visit and group main effects (Repeated-measures ANOVA p=0.025 and <0.001 for visit and group respectively) and a significant interaction between visit and group (p=0.031). At all study visits, the symptomatic group had lower thresholds (higher sensitivity) than the asymptomatic group (Tukey HSD all p<0.015) while the difference between symptomatic and control groups was significant at the 2-week lens-wearing visit (Tukey HSD p=0.027).

EXAMPLE 2

Responses to Repetitive Cool Pneumatic Stimuli in Symptomatic, Asymptomatic, and Non-Contact Lens Wearers Following determination of threshold levels of cool pneumatic stimulus for each subject as described in Example 1, threshold, subthreshold and suprathreshold (25% below and above threshold, respectively) sessions occurred in random order, with a 5-minute break between sessions. In each session, 20 equal-intensity, 2-second trials were presented, with approximately 10 second inter-stimulus intervals. Following each stimulus, subjects rated the intensity using a 5-point scale: 0, no stimulus; 1, very mild; 2, mild; 3, moderately strong; and 4, strong stimulus.

Figure 3:
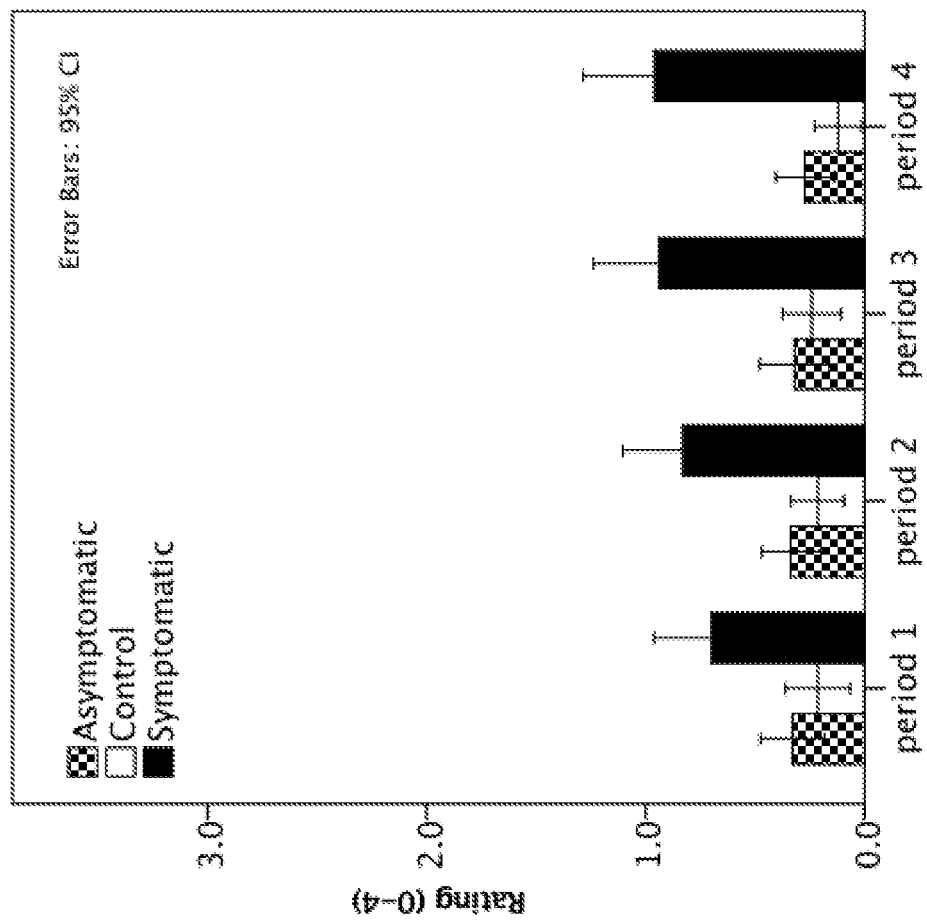
FIG. 3 is a graph of adaptation and sensitization of contact lens wearers to subthreshold pneumatic stimuli.
Figure 4:
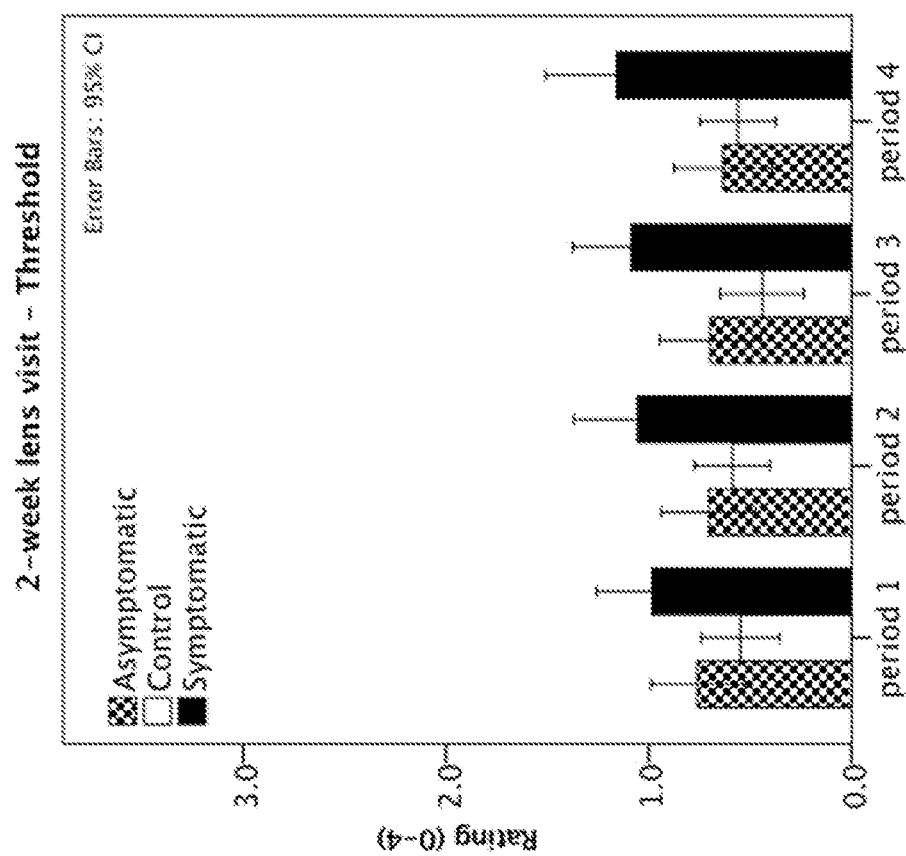
FIG. 4 is a graph of adaptation and sensitization of contact lens wearers to threshold pneumatic stimuli.
Figure 5:
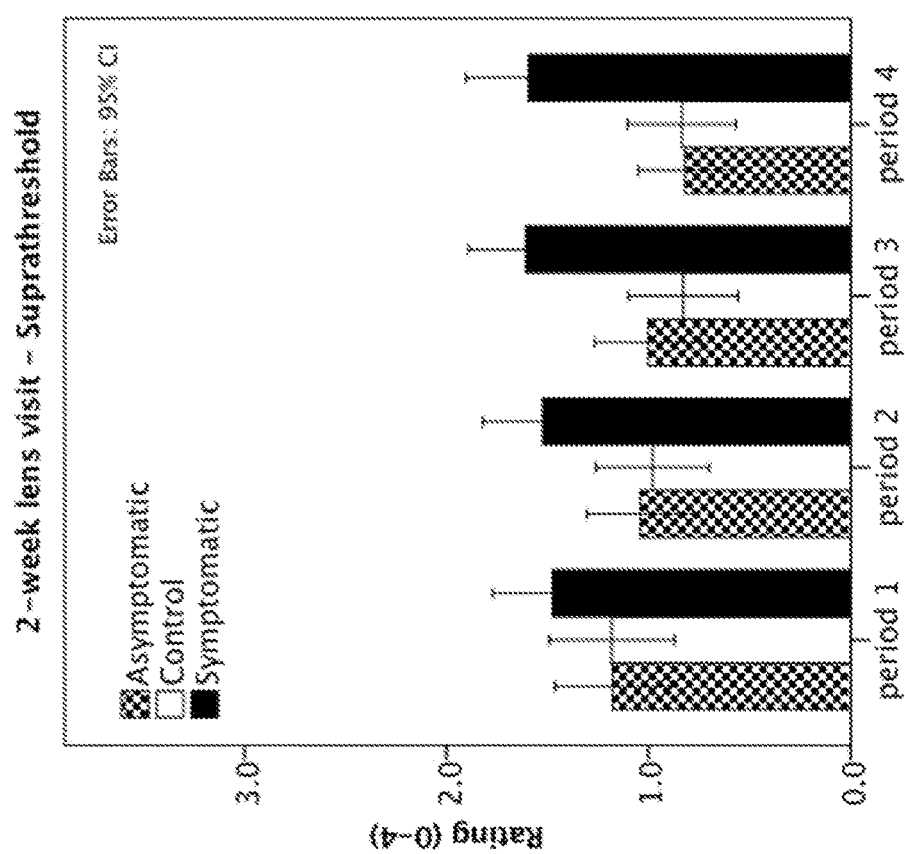
FIG. 5 is a graph of adaptation and sensitization of contact lens wearers to suprathreshold pneumatic stimuli.

Table 4 lists the average ratings during the four time periods for each intensity level at each visit, stratified by group. FIGS. 3-5 depict the data from the 2-week lens wear (CL) visit.

TABLE 4

| | Control | | | Asymptomatic | | | Symptomatic | | |
|---|---|---|---|---|---|---|---|---|---|
| Visit | Sub-th | Thresh. | Supra-th | Sub-th | Thresh. | Supra-th | Sub-th | Thresh. | Supra-th |
| BL2-P1 | 0.4 ± 0.4 | 0.7 ± 0.6 | 1.2 ± 0.8 | 0.2 ± 0.2 | 0.7 ± 0.6 | 1.2 ± 0.6 | 0.8 ± 0.6 | 1.1 ± 0.7 | 1.5 ± 0.7 |
| BL2-P2 | 0.4 ± 0.4 | 0.8 ± 0.6 | 1.1 ± 0.5 | 0.2 ± 0.3 | 0.7 ± 0.6 | 1.0 ± 0.7 | 0.8 ± 0.7 | 1.0 ± 0.8 | 1.4 ± 0.8 |
| BL2-P3 | 0.3 ± 0.4 | 0.8 ± 0.5 | 1.0 ± 0.6 | 0.2 ± 0.3 | 0.6 ± 0.5 | 0.8 ± 0.7 | 0.9 ± 0.6 | 1.1 ± 0.8 | 1.4 ± 0.8 |
| BL2-P4 | 0.4 ± 0.5 | 0.7 ± 0.7 | 1.0 ± 0.7 | 0.2 ± 0.3 | 0.6 ± 0.5 | 0.9 ± 0.7 | 1.0 ± 0.6 | 1.2 ± 0.7 | 1.2 ± 0.7 |
| NL-P1 | 0.4 ± 0.5 | 0.7 ± 0.4 | 1.1 ± 0.6 | 0.3 ± 0.4 | 0.7 ± 0.4 | 1.0 ± 0.4 | 0.6 ± 0.5 | 1.0 ± 0.5 | 1.5 ± 0.8 |
| NL-P2 | 0.4 ± 0.4 | 0.5 ± 0.4 | 1.2 ± 0.7 | 0.3 ± 0.4 | 0.6 ± 0.4 | 1.1 ± 0.5 | 0.7 ± 0.6 | 1.0 ± 0.6 | 1.4 ± 0.7 |
| NL-P3 | 0.3 ± 0.4 | 0.6 ± 0.4 | 1.0 ± 0.7 | 0.4 ± 0.3 | 0.6 ± 0.5 | 1.1 ± 0.6 | 0.7 ± 0.6 | 1.1 ± 0.7 | 1.5 ± 0.7 |
| NL-P4 | 0.2 ± 0.3 | 0.5 ± 0.5 | 0.9 ± 0.5 | 0.2 ± 0.3 | 0.6 ± 0.6 | 1.0 ± 0.7 | 0.7 ± 0.6 | 1.0 ± 0.5 | 1.3 ± 0.6 |
| CL-P1 | 0.2 ± 0.3 | 0.5 ± 0.3 | 1.2 ± 0.6 | 0.3 ± 0.4 | 0.8 ± 0.6 | 1.2 ± 0.7 | 0.7 ± 0.6 | 1.0 ± 0.6 | 1.5 ± 0.7 |
| CL-P2 | 0.2 ± 0.2 | 0.6 ± 0.3 | 1.0 ± 0.5 | 0.3 ± 0.3 | 0.7 ± 0.6 | 1.0 ± 0.6 | 0.8 ± 0.6 | 1.1 ± 0.7 | 1.5 ± 0.7 |
| CL-P3 | 0.2 ± 0.2 | 0.4 ± 0.4 | 0.8 ± 0.5 | 0.3 ± 0.4 | 0.7 ± 0.6 | 1.0 ± 0.6 | 0.9 ± 0.7 | 1.1 ± 0.7 | 1.6 ± 0.7 |
| CL-P4 | 0.1 ± 0.2 | 0.6 ± 0.3 | 0.8 ± 0.5 | 0.3 ± 0.3 | 0.6 ± 0.6 | 0.8 ± 0.6 | 1.0 ± 0.8 | 1.2 ± 0.8 | 1.6 ± 0.7 |

At baseline, there was a significant difference in overall average ratings between intensity levels (RMANOVA intensity main effect p<0.001) and the differences between periods depended on the intensity level (RMANOVA intensity and period interaction p=0.004). For sub-threshold and threshold stimuli, the average ratings over the four periods were approximately equal except in the symptomatic group while the average ratings at supra-threshold levels decreased over the four periods. At the no-lens visit, a significant difference in average ratings was found between stimulus levels (RMANOVA p<0.001).

Similar to the baseline, there was a significant difference in overall average ratings between intensity levels (RMANOVA p<0.001) after resuming the lens wearing for 2 weeks. Also, the differences between periods depended on the intensity level and group (RMANOVA p=0.020 and 0.001, respectively). The average ratings seemed to be constant or decreased over the four periods in asymptomatic and control groups while the symptomatic group ratings tended to increase over the periods. For all stimulus levels at each visit, the average ratings in the symptomatic group were higher than those of asymptomatic group (all p<0.001) and control group (Tukey HSD p=0.024, 0.005 and <0.001 for BL, NL and 2wkL respectively). There were no significant differences in ratings between the asymptomatic and control groups (all p>0.05).

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method of determining a predisposition to contact lens discomfort in a patient, said method comprising:
   determining a detection threshold of the patient by delivering a cool mechanical stimulus to the cornea of the patient;
   optionally applying a series of cool mechanical stimuli to the cornea of the patient; and
   classifying the patient as being predisposed to contact lens discomfort if
   (i) the detection threshold is at or below a cut-off value predetermined to be associated with predisposition to contact lens discomfort,
   (ii) the patient does not adapt to the series of cool mechanical stimuli, or
   (iii) the detection threshold is at or below a cut-off value predetermined to be associated with predisposition to contact lens discomfort and the patient does not adapt to the series of cool mechanical stimuli.

2. The method of claim 1, comprising applying a series of cool mechanical stimuli to the cornea of the patient and classifying the patient as being predisposed to contact lens discomfort if the patient does not adapt to the series of cool mechanical stimuli.

3. The method of claim 1, wherein the cool mechanical stimulus is delivered by directing a cool fluid to the cornea of the patient.

4. The method of claim 3, wherein the cool fluid is a gas.

5. The method of claim 3, wherein the cool fluid is a liquid.

6. The method of claim 2, wherein the cool mechanical stimulus is a cool pneumatic stimulus and the series of cool mechanical stimuli is a series of cool pneumatic stimuli.

7. The method of claim 6, wherein the cool pneumatic stimulus is delivered by a pneumatic esthesiometer.

8. The method of claim 6, wherein the cool pneumatic stimulus is delivered at about room temperature.

9. The method of claim 6, wherein the cool pneumatic stimulus is delivered to the cornea at a controlled flow rate having a temperature of from about 20° C. to 30° C. from an air pulse source located at a controlled spaced-apart distance of from 1 mm to 10 mm from the cornea for a controlled duration of from 1 second to 5 seconds.

10. The method of claim 6, wherein the cool pneumatic stimulus is delivered as ascending intensities of air pulse flow rates, with a pause between deliveries of different air pulse flow rates, until an air pulse flow rate elicits a positive psychophysical response from the patient, wherein said air pulse flow rate that elicits the positive psychophysical response from the patient is used to determine the patient's detection threshold.

11. The method of claim 6, wherein the series of cool pneumatic stimuli is applied to the cornea of the patient and the patient is classified as being predisposed to contact lens discomfort if the patient does not adapt to the series of cool pneumatic stimuli.

12. The method of claim 11, wherein the series of cool pneumatic stimuli is applied at subthreshold intensity.

13. The method of claim 11, wherein the series of cool pneumatic stimuli is applied at threshold intensity.

14. The method of claim 11, wherein the series of cool pneumatic stimuli is applied at suprathreshold intensity.

15. The method of claim 11, wherein the patient is prescribed initial contact lenses after the detection threshold is determined and the series of cool pneumatic stimuli is applied to the patient after the initial contact lenses have been worn by the patient for at least one day.

16. The method of claim 15, further comprising prescribing contact lenses comprising a different design and/or material from the initial contact lenses if the patient does not adapt to the series of cool pneumatic stimuli.

17. The method of claim 2, wherein the detection threshold or the patient's ability to adapt to the series of cool mechanical stimuli are determined prior to prescribing contact lenses to the patient.

18. The method of claim 1, wherein the patient is one of a neophyte contact lens wearer, a current contact lens wearer and a lapsed contact lens wearer.

19. The method of claim 1, further comprising including the patient as a subject in a clinical trial for a pre-marketed contact lens.

20. The method of claim 1, wherein classifying the patient comprises inputting results of the determining step into a system comprising a controller configured to i) receive the results; ii) optionally receive data on whether the patient adapts to a series of cool mechanical stimuli administered to an ocular surface of the patient; and iii) classify the patient as being predisposed to contact lens discomfort if the patient's detection threshold is below a predetermined cut-off associated with predisposition to contact lens discomfort and/or if the patient does not adapt to the series of cool mechanical stimuli.

21. The method of claim 20, wherein the controller carries out the additional step of iv) outputting a recommendation for the patient's follow-up management based on the patient's classification.

22. The method of claim 21, wherein the patient is classified as being predisposed to contact lens discomfort and the recommendation for the patient's follow-up management comprises at least one of prescribing a premium lens to the patient, prescribing an ophthalmic drop that promotes ocular comfort, and scheduling a follow-up visit for the patient.

23. An analysis system comprising:
- an esthesiometer comprising a source of fluid, a fluid flow rate controller coupled to the source of fluid, a tip coupled to the flow rate controller adapted to deliver a cool mechanical stimulus to an ocular surface of a patient, and a user input device by which patient responses can be signaled; and
- a controller in communication with the flow rate controller to execute a test process including:
  - i) producing a stimulus according to a detection threshold test protocol for detecting a threshold of a cool mechanical stimulus administered to an ocular surface of the patient, and storing patient responses received at the user input device during execution of the detection threshold test protocol, the sequence controller determining the patient's detection threshold based on the stored patient responses for the detection threshold protocol;
  - ii) optionally producing a series of stimuli according to an adaptation test protocol for determining whether the patient adapts to a series of cooling mechanical stimuli administered to the ocular surface of the patient, and storing patient responses received at the user input device during execution of the adaptation test protocol, the controller determining whether the patient adapts to the series of cooling mechanical stimuli based on the stored patient responses for the adaptation test protocol; and
  - iii) generating data for classifying the patient as being predisposed to contact lens discomfort if the patient's detection threshold is below a predetermined cut-off associated with predisposition to contact lens discomfort and/or if the patient does not adapt to the series of cooling mechanical stimuli.

24. The analysis system of claim 23, wherein the fluid is a gas, the cooling mechanical stimulus is a cool pneumatic stimulus, and the series of cooling mechanical stimuli is a series of pneumatic cooling stimuli.

* * * * *